United States Patent
Westbrook

(10) Patent No.: US 10,234,385 B2
(45) Date of Patent: Mar. 19, 2019

(54) OPTICAL SENSOR HAVING FIDUCIARY MARKS DETECTED BY BACKSCATTERED LIGHT

(71) Applicant: OFS Fitel, LLC, Norcross, GA (US)

(72) Inventor: Paul S Westbrook, Bridgewater, NJ (US)

(73) Assignee: OFS FITEL, LLC, Norcross, GA (US)

( * ) Notice: Subject to any disclaimer, the term of this patent is extended or adjusted under 35 U.S.C. 154(b) by 186 days.

(21) Appl. No.: 15/267,494

(22) Filed: Sep. 16, 2016

(65) Prior Publication Data

US 2017/0003219 A1 Jan. 5, 2017

Related U.S. Application Data

(63) Continuation-in-part of application No. 14/201,993, filed on Mar. 10, 2014, now Pat. No. 9,470,588.

(60) Provisional application No. 61/786,863, filed on Mar. 15, 2013.

(51) Int. Cl.
*G02B 6/02* (2006.01)
*G01N 21/47* (2006.01)
*G01L 1/24* (2006.01)

(52) U.S. Cl.
CPC ............ *G01N 21/474* (2013.01); *G01L 1/242* (2013.01); *G01N 21/4785* (2013.01); *G02B 6/02042* (2013.01); *G01N 2021/4709* (2013.01); *G01N 2021/4742* (2013.01)

(58) Field of Classification Search
CPC ............ G01N 21/474; G01N 21/4785; G01N 2021/4709; G01N 2021/4742; G01L 1/242; G02B 6/02042
See application file for complete search history.

(56) References Cited

U.S. PATENT DOCUMENTS 9,909,903 B2 * 3/2018 Lewis ................ G01D 5/35358

* cited by examiner

*Primary Examiner* — John Bedtelyon

(57) ABSTRACT

An optical fiber having at least one fiduciary mark is provided. The at least one fiduciary mark is located at one or more axial positions along the optical fiber. The at least one fiduciary mark is configured to produce at least one change in a backscattering signal in the optical fiber. The at least one change in a backscattering signal may be an abrupt change in the backscattering signal. The abrupt change in the backscattering signal occurs over a length of the optical fiber that is of the order of or less than a spatial resolution of an interrogation system employed to detect the backscattering signal.

22 Claims, 4 Drawing Sheets

OPTICAL SENSOR HAVING FIDUCIARY MARKS DETECTED BY BACKSCATTERED LIGHT

CROSS-REFERENCE TO RELATED APPLICATIONS

This application is a Continuation-In-Part of Non-Provisional U.S. patent application Ser. No. 14/201,993, which was filed on Mar. 10, 2014 and has the title "OPTICAL SENSOR HAVING FIDUCIARY MARKS DETECTED BY RAYLEIGH SCATTERED LIGHT."

BACKGROUND OF THE INVENTION

1. Field of the Invention

The invention relates generally to optical fibers. More specifically, the invention relates to an optical sensor that employs backscattering to determine a location in the fiber sensor.

2. Discussion of the Related Art

Optical fibers have been employed in sensing applications, including measurements of distributed strain and temperature in an optical fiber as well as acoustic signals impinging on the fiber. In one sensing application, an optical signal is transmitted into the optical fiber and perturbations in the fiber core(s) result in back scatter which may be analyzed to obtain the shape of the fiber. In another, the distributed scattering signal provides a measurement of acoustic waves that act to strain the fiber. In such distributed sensors, measurements may be performed at any part of the array. Thus continuous measurements with a certain spatial resolutions are possible along the distributed sensor.

One type of back scattering that has been proposed for use in fiber shape measurements is Rayleigh back scattering. Unfortunately, the spectral and spatial response of Rayleigh back scattering is random. Further, localization of the signal requires precise knowledge of a group index of a fiber. This limits the reliability of Rayleigh back scattering in distributed sensing applications. If there is more than one core in the optical fiber, an additional problem arises. It is necessary to correlate the Rayleigh back scattered signal from the multiple cores in order to obtain an accurate estimate of the fiber shape. However, this also requires accurate knowledge of the group index variation between as well as along the different cores. More particularly, the task of reconstructing the shape requires a measurement of the exact position from backscatter in the fiber. Typically, this will depend on the effective index of a mode propagating in a core of the fiber and, in particular, on the group index of the propagating mode. The group index permits a conversion of temporal and frequency domain information obtained into spatial domain information. However, the effective index and group index will not be the same in all cores of a multicore fiber. Moreover, the effective index and group index will not be the same for both polarizations.

Related art techniques to overcome this problem require accurate calibration of the propagation of light in each core of a multicore fiber. Unfortunately, any drift in waveguide properties can render inaccurate any such calibration. Another related art technique involves the use of fiber gratings to provide the scattering. However, this technique requires the inscription of fiber gratings along the entire length of the fiber. Such fabrication adds cost and complexity to a fiber sensor.

Thus, a need remains in the art to improve measurements of distance along an optical fiber using optical backscatter that does not require continuous fiber gratings or absolute calibration stability.

BRIEF SUMMARY OF THE INVENTION

The above-described problems are addressed and a technical solution is achieved in the art by providing an optical sensor comprising an optical fiber having at least one fiduciary mark. As used herein, a fiduciary mark is an alteration of a physical property at a known location in the optical fiber used in a distributed sensor such that there is an observable change at the known location in a backscattering pattern produced in response to a signal/light introduced into the optical fiber at one end. Preferably, the backscattering pattern is Rayleigh scattering pattern. Furthermore, the fiduciary mark is placed in the fiber during a fiber or sensor manufacturing. The fiduciary mark may comprise any measurable variation in the backscattering signal and on a length scale comparable to the required length accuracy of the sensing system. In one example, the fiduciary mark may be configured to produce an abrupt change in a backscattering signal in the optical fiber in response to an incoming signal/light. Such marks are operable to change the backscattering amplitude and phase in an abrupt manner so that they appear clearly in a spatial trace of a backscattering response. An abrupt change is defined as a change that occurs over a length that is on the order of, or less than, a spatial resolution of an interrogation system used to detect the backscattering response. This abrupt change may have an amplitude that is sufficiently large compared to fluctuations in backscattering response such that it can be distinguished from such fluctuations.

More particularly, the above-described problems are addressed and a technical solution is achieved in the art by providing an optical fiber having at least one fiduciary mark. The at least one fiduciary mark is located at one or more axial positions along the optical fiber. The at least one fiduciary mark is configured to produce at least one change in a backscattering signal in the optical fiber.

The at least one change in a backscattering signal may be an abrupt change in the backscattering signal. The abrupt change in the backscattering signal may occur over a length of the optical fiber that is of the order of or less than a spatial resolution of an interrogation system employed to detect the backscattering signal. In an example, the optical fiber comprises at least two cores.

In another example, the at least one change in the backscattering signal may be equal to or greater than a length measurement accuracy in the optical fiber.

In an example, the at least one fiduciary mark may be located at a known axial position along the optical fiber. The at least one fiduciary mark may correspond to a fiduciary mark located at the same position in two or more cores of a multicore fiber. In an example, the at least one fiduciary mark may be identified as a common fiduciary mark when at least one Rayleigh backscattering signal produced in one core of the two or more cores is substantially cross-correlated with at least one other Rayleigh backscattering signal produced in another core of the two or more cores.

The change in a backscattering signal may be produced by an alteration to propagation properties of the optical fiber over substantially the same distance along the optical fiber. The change in a backscattering signal may be a change in at least one of an intensity, amplitude, polarization dependence, or phase of the backscattering signal. The alteration to propagation properties may be an induced loss or an induced gain in the backscattering signal relative to a background noise signal.

In an example, the at least one fiduciary mark may be produced by exposure of the optical fiber to actinic radiation during a manufacturing process of the fiber or the sensor. In another example, the at least one fiduciary mark may be produced by at least one of a thermal, an electrical, a strain, a poling, or a tapering perturbation of the optical fiber introduced during a manufacturing process. The fiduciary mark may be produced by splicing two fibers with different Rayleigh scattering properties (e.g., with different Rayleigh scattering strengths). The at least one fiduciary mark may be produced during a draw process of the optical fiber. In an example, the at least one fiduciary mark may be introduced in a core and/or a cladding of the optical fiber. In another example, the actinic radiation may be sufficiently intense to partially damage the waveguide material, resulting in additional back scattering and possibly greater loss at that location.

The at least one fiduciary mark may be configured to produce an aperiodic pattern, a quasi-periodic pattern, or a periodic pattern of altered backscattering. Individual parts of the aperiodic pattern, the quasi-periodic pattern, or the periodic pattern of altered backscattering may comprise abrupt changes in backscattering.

In an example, the at least one fiduciary mark may comprise an aperiodic set, a quasi-periodic set, or a periodic set of fiduciary marks in a plurality of cores when the optical fiber is a multicore fiber, wherein the aperiodic, quasi-periodic, or periodic fiduciary marks are at least one of unequal length, unequal spacing, or operable to produce an unequal change in the backscattering signal. A set of fiduciary marks may be operable to provide identifying information about a region where the at least one fiduciary mark is located. The identifying information about a region where the at least one fiduciary mark is located may identify a code indicating where the at least one fiduciary mark is located.

In another example, the at least one fiduciary mark may comprise an aperiodic set, a quasi-periodic set, or a periodic set of fiduciary marks in a plurality of cores when the optical fiber is a multicore fiber, wherein the aperiodic set, quasi-periodic set, or periodic set of fiduciary marks induces the same pattern in two or more cores of the plurality of cores. In another example, the at least one fiduciary mark may comprise a plurality of aperiodic sets, quasi-periodic sets, or periodic sets of fiduciary marks in a plurality of cores when the optical fiber is a multicore fiber, wherein at least two of the aperiodic sets, quasi-periodic sets, or periodic sets induces the same pattern at the same position in two or more cores of the plurality of cores. The above-described problems are addressed and a technical solution is achieved in the art by providing a method of sensing a location in an optical sensor. A light signal is introduced into an optical fiber comprising at least two cores. Rayleigh backscattering signals located at one or more axial positions in the at least two cores of the optical fiber are measured. At least one change in the measured Rayleigh backscattering signals in the at least two cores of the optical fiber are detected. The measured Rayleigh backscattering signals corresponding to at least one fiduciary mark in the at least two cores of the optical fiber are cross-correlated. The at least one fiduciary mark is identified as a fiduciary mark common to the at least two cores when the measured Rayleigh backscattering signals are substantially correlated.

BRIEF DESCRIPTION OF THE DRAWINGS

The present invention may be more readily understood from the detailed description of an exemplary embodiment presented below considered in conjunction with the attached drawings and in which like reference numerals refer to similar elements and in which.

It is to be understood that the attached drawings are for purposes of illustrating the concepts of the invention and may not be to scale.

DETAILED DESCRIPTION OF THE INVENTION

Figure 1:
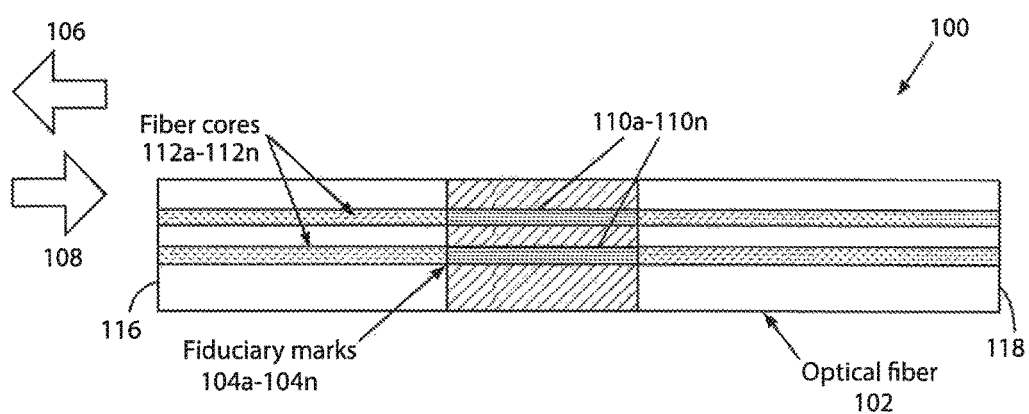
FIG. 1 is a perspective view of one embodiment of an optical sensor.

FIG. 1 is a perspective view of one embodiment of an optical sensor 100. The optical sensor 100 comprises an optical fiber 102 having at least one fiduciary mark 104a-104n. The at least one fiduciary mark 104a-104n is configured to produce an abrupt change in a backscattering signal 106 in the optical fiber 102 in response to an incoming signal/light 108. Preferably, the backscattering signal 106 is a Rayleigh backscattering signal. one example, the at least one fiduciary mark 104a-104n is operable to change the amplitude and phase of a resulting backscattering signal in an abrupt manner that appears clearly in a spatial trace of the backscattering response.

An abrupt change is defined as a change that occurs over a length of the optical fiber 102 that is on the order of, or less than, the spatial resolution of an interrogation system used to detect the backscattering response. This abrupt change may have an amplitude that is sufficiently large compared to fluctuations in a backscattering response signal such that it can be distinguished from such fluctuations. The abrupt change in a backscattering signal may be produced by an alteration to propagation properties of the optical fiber 102 over substantially the same distance along the optical fiber 102. The abrupt change in a backscattering signal may be an abrupt change in at least one of an intensity, amplitude, polarized dependence, or phase of the backscattering signal. The alteration to propagation properties may an induced loss or induced gain in the backscattering signal relative to backscattering signal away from the mark.

In another example, the at least one change in the backscattering signal may be equal to or greater than a length measurement accuracy in the optical sensor 100. Generally, the length measurement accuracy in the optical sensor 100 is the same as (or greater than) the resolution. If it is greater, then fiduciary marks 104a-104n may be made that are greater than the resolution as long as long as the resulting fiduciary marks 104a-104n may be employed to locate positions in the fiber to the required length measurement accuracy.

In one example, a fiduciary mark (e.g., 104*a*) may be a smooth slow change over a length greater than the system resolution. For instance, if a fiduciary mark (e.g., 104*a*) is a 1 cm Gaussian shaped bump in the Rayleigh intensity, then it may still be useful if employed in applications where only 1 cm level position accuracy is needed or where the fiber length is very long.

The at least one fiduciary mark 104*a*-104*n* may be located at one or more axial positions 110*a*-110*n* along the optical fiber 102. In an example, fiduciary marks 104*a*-104*n* may be placed in at least two of two or more cores 112*a*-112*n* at a common (e.g., the same) known axial position (e.g., 110*a*). In another example, the common fiduciary marks 104*a*-104*n* may be displaced from each other by a known distance. In another example, the at least one fiduciary mark 104*a*-104*n* may be introduced in a cladding of the optical fiber 102. Although the figure shows multiple cores 112*a*-112*n*, the at least one fiduciary mark 104*a*-104*n* may be located at one or more axial positions along the optical fiber 102 regardless of the number of cores in the optical fiber 102. The at least one fiduciary mark 104*a*-104*n* is configured to produce at least one change in a backscattering signal in the optical fiber 102. Preferably, the backscattering signal is a Rayleigh backscattering signal.

Figure 2:
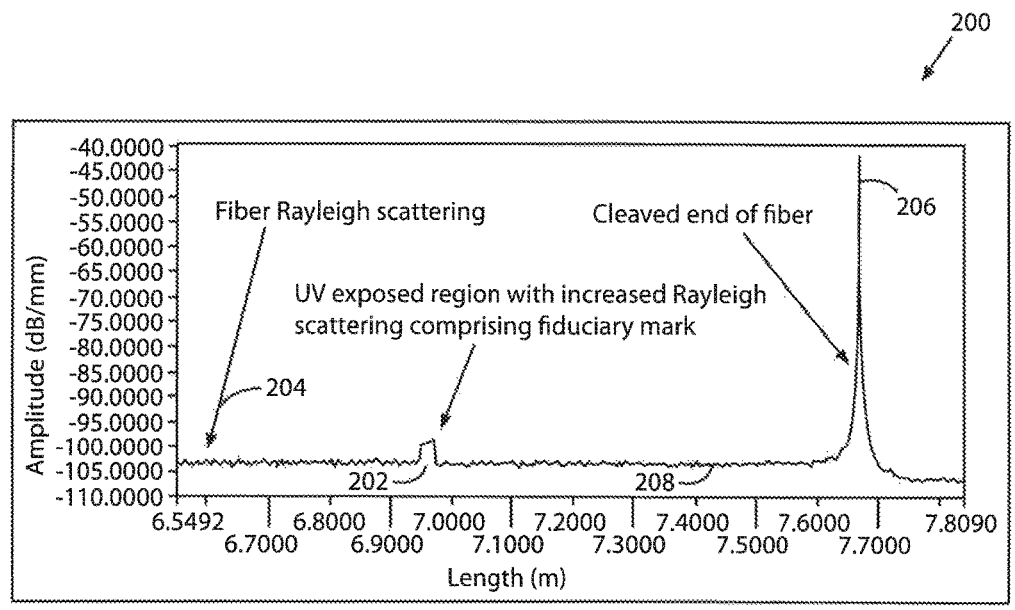
FIG. 2 shows a trace of Rayleigh back scattering signal power measured with a commercial spectral interferometric system from a single core fiber.

FIG. 2 shows a trace 200 of fiber Rayleigh backscattering signal power from a single core fiber measured with a commercial spectral interferometric system (e.g., LUNA OBR). The y-axis is the Rayleigh back scattered power. The x-axis is position along the optical fiber 102. Such devices measure all back scattered power over a certain wavelength range. In most fibers the back scattered signal is predominantly the result of Rayleigh scattering from index perturbations in the core of the fiber. However, other scattering mechanisms can also contribute to the back scattered signal. These include imperfections of the core-cladding boundary, impurities in the core or cladding material, defects in the glass matrix, density fluctuations, and even large imperfections, e.g., cracks or gas bubbles, in the glass matrix in the core or cladding. The back scattering trace 200 shows a change 202 (e.g., produced by a fiduciary mark) induced in a Rayleigh back scattering response signal 204 responsive to a light signal 108 introduced at one end 116 of the optical fiber 102. Note that, in an example, the change 202 is comprised of two changes. One change is an increase in Rayleigh scattering and one change is a decrease in Rayleigh scattering. Thus, the change 202 may be considered two fiduciary marks, or it may be considered as one fiduciary mark with two changes. Also shown is a signal response peak 206 produced at a second end 118 (e.g., a cleaved end 118) of the optical fiber 102. Referring to FIGS. 1 and 2, a measurement of the Rayleigh back scattering response signal 204 intensity may exhibit a change 202 in each of the two of two or more cores 112*a*-112*n*.

One method of introducing a fiduciary mark that is operable to induce a change 202 in each of the two of two or more cores 112*a*-112*n* in a Rayleigh back scattering response signal 204 is through actinic radiation exposure: for example, UV irradiation of a core of an optical fiber, such as a Ge doped core. To demonstrate this, the single-core optical fiber of FIG. 2 was irradiated by a 2.5 cm beam of 248 nm UV radiation in a post-draw process after the fiber had been fabricated.

When such UV irradiation is used to expose a multicore fiber (e.g., the optical fiber 102), a similar mark may appear in all of the cores 110*a*-110*n* of the multicore fiber (e.g., the optical fiber 102). Any subsequent measurement of the Rayleigh back scattering response from more than one core (e.g., 112*a*, 112*b*) may exhibit such a mark at a precise axial position along the optical fiber 102 that is common to all cores 112*a*-112*n*.

Since the change 202 is known to occur at the same location in each core (e.g., 110*a*, 110*b*), the change 202 can be used to precisely overlap spatial information obtained from the two or more cores 112*a*-112*n* over an entire length of the optical fiber 102.

In one example, the amplitude of the change 202 in the intensity of the Rayleigh back scattering response signal 204 may be identified as a fiduciary mark if it differs from the background fluctuations 208 of the Rayleigh back scattering response signal 204 by at least 2 dB. In another example, the change 202 may be identified as common fiduciary mark when at least one Rayleigh backscattering signal response produced in one core (e.g. 112*a*) of two or more cores 112*a*-112*n* is substantially cross-correlated with at least one other Rayleigh backscattering signal response produced in another core (e.g. 112*b*) of the two or more cores. In an example, the calculated cross-correlated amplitude of the Rayleigh back scattering signal intensity may be identified as a fiduciary mark if it differs from the calculated cross-correlated amplitude of the background fluctuations 208 of the Rayleigh back scattering signal response 204 by at least 3 dB.

Thus, a fiduciary mark can be used to spatially correlate information in two or more cores 112*a*-112*n* of an optical fiber 102 without the requirement of stable, precisely characterized values of group index along the optical fiber 102 and across different cores of the two or more cores 112*a*-112*n*. In an example, the two or more cores 112*a*-112*n* of the optical fiber 102 may have different effective indices and/or different group indices. Further, at least one core (e.g., 112*a*) of the two or more cores 112*a*-112*n* of the optical fiber 102 may support more than one mode of propagation.

Analysis of the phase of the Rayleigh back scattering response signal 204 using interferometric techniques may be used to obtain the strain state of the two or more cores 112*a*-112*n* of the optical fiber 102 and hence the local state of twist and bend of the optical fiber 102. This information may be integrated to obtain the shape of the optical fiber 102. From the obtained shape, a position of any point along the optical fiber 102 may be obtained; more particularly, a location of the second end 118 of the optical fiber 102 distal to the first end 116 may be obtained, which may contain a probe or actuator that performs a desired task.

UV irradiation is not the only means of introducing such a mark. Other processing methods such as thermal, electrical, strain, poling and tapering are also possible. Use of actinic radiation, air jets or other thermal and mechanical processes during the draw process is also possible. Splicing of differing fibers can also yield such marks in a length of fiber comprising one or more splices.

Figure 3:
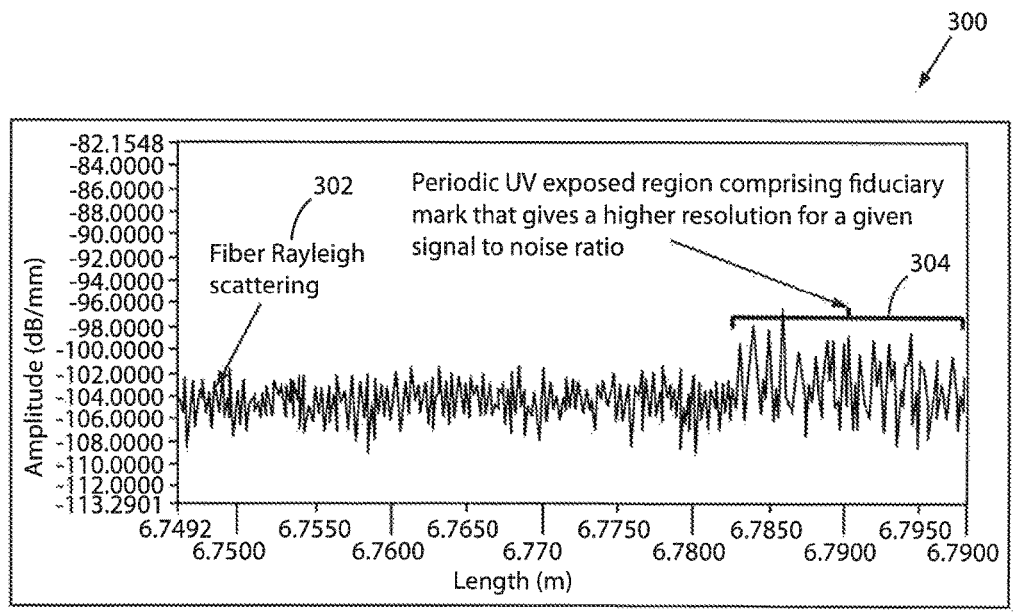
FIG. 3 is a Rayleigh back scattering trace showing a back scattering response in a single core fiber induced by a modulated fiduciary mark comprised of many individual exposures to actinic radiation.

FIG. 3 is a Rayleigh back scattering trace 300 from a single core fiber showing a back scattering response 302 induced by a modulated fiduciary mark comprised of many individual exposures to actinic radiation. The many individual exposures to actinic radiation may induce a periodic or quasi-periodic pattern of irradiation that results in a corresponding periodic or quasi-periodic pattern 304 in the response 302. In such circumstances, the resulting fiduciary marks may be correlated with higher resolution than would be possible with a single fiduciary mark.

Figure 4:
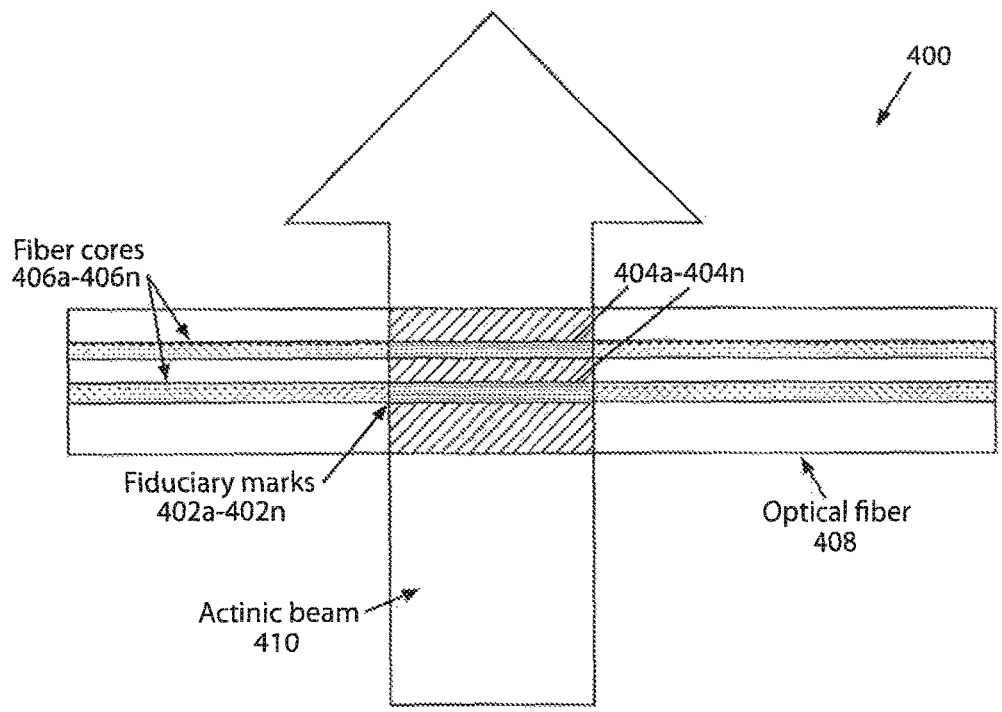
FIG. 4 is a schematic diagram illustrating one method of imprinting fiduciary marks at the same location in two or more cores of a multicore fiber using an actinic radiation beam.

FIG. 4 is a schematic diagram illustrating one method 400 of imprinting fiduciary marks 402*a*-402*n* at the same location 404*a*-404*n* in two or more cores 406*a*-406*n* of a multicore fiber 408 using an actinic radiation beam 410. The two or more cores 406a-406n of a multicore fiber 408 are exposed at a substantially perpendicular angle to the actinic radiation beam 410. The actinic radiation beam 410 may be, but is not limited to, for example, an ultraviolet (UV) 248 nm radiation beam, an infrared (IR) femtosecond radiation beam, or a CO2 laser beam. The fiduciary marks may be imprinted during the fiber fabrication process, or during a post-draw process during which the sensor is manufactured. In a preferred embodiment, the actinic beam is a single beam. The beam may be very long along the length of the fiber, however, it may also be very short in width along the fiber. For instance, a UV beam with a wavelength of 0.248 microns can be focused to a 20 micron width along the fiber axis using commercial lenses. No matter what the beam width is, if desired, the fiduciary mark may be made longer the size of the beam by scanning the beam along the fiber, moving the fiber, or both, so that the actinic exposed region is longer than the beam width and in fact can be arbitrarily long.

Figure 5:
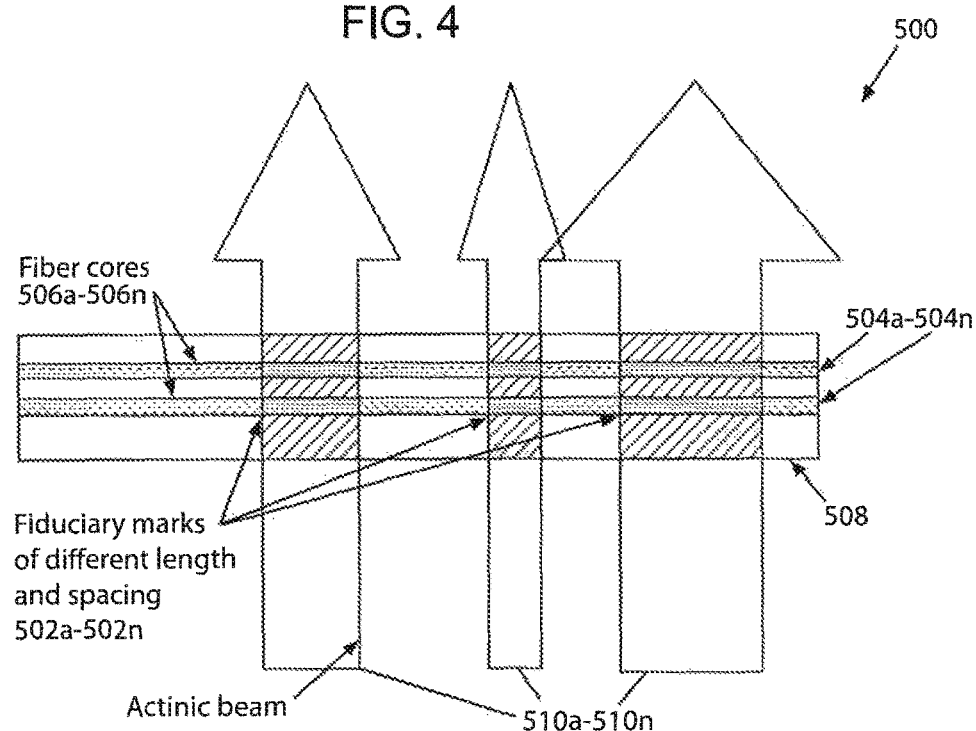
FIG. 5 is a schematic diagram illustrating one method of imprinting fiduciary marks at the same location in two or more cores of a multicore fiber using a plurality of actinic radiation beams; and, FIG. 6 is a process flow detailing a method of sensing a location in an optical sensor.

FIG. 5 is a schematic diagram illustrating one method 500 of imprinting fiduciary marks 502a-502n at the same location 504a-504n in two or more cores 506a-506n of a multicore fiber 508 using a plurality of actinic radiation beams 510a-510n. In an example, the two or more cores 506a-506n of a multicore fiber 508 are exposed at a substantially perpendicular angle to the plurality of actinic radiation beams 510a-510n. The plurality of actinic radiation beams 510a-510n may be equally spaced to induce a periodic set of fiduciary marks. In another example, the plurality of actinic radiation beams 510a-510n may be unequally spaced, may be of unequal length, or may be of unequal intensity to induce an aperiodic set, a quasi-periodic set, or a periodic set of fiduciary marks 502a-502n at the same location 504a-504n in the two or more cores 506a-506n of the multicore fiber 508. The resulting induced set of fiduciary marks 502a-502n may induce a corresponding unequal spacing, unequal length, or unequal in magnitude/phase of changes in a Rayleigh back scattering response to an incoming light, respectively. In another example, the resulting induced set of fiduciary marks 502a-502n may comprise an aperiodic set, a quasi-periodic set, or a periodic set of fiduciary marks in a plurality of the cores 506a-506n when the optical fiber 102 is a multicore fiber 508, where the aperiodic set, quasi-periodic set, or periodic set of fiduciary marks 502a-502n induces the same pattern in two or more cores of the plurality of cores 506a-506n. In another example, the resulting induced set of fiduciary marks 502a-502n may comprise a plurality of aperiodic sets, quasi-periodic sets, or periodic sets of fiduciary marks 502a-502n in a plurality of cores 506a-506n when the optical fiber 102 is a multicore fiber 508, where at least two aperiodic sets, quasi-periodic sets, or periodic sets of fiduciary marks 502a-502n induces the same pattern at the same position in two or more cores of the plurality of cores 506a-506n.

In another example, a set of fiduciary marks 502a-502n may be configured to provide a code indicating where the set of fiduciary marks 502a-502n is located or some other identifying information about the region where the set of fiduciary marks 502a-502n is located. For instance, the set of fiduciary marks 502a-502n may represent digits of a number.

Figure 6:
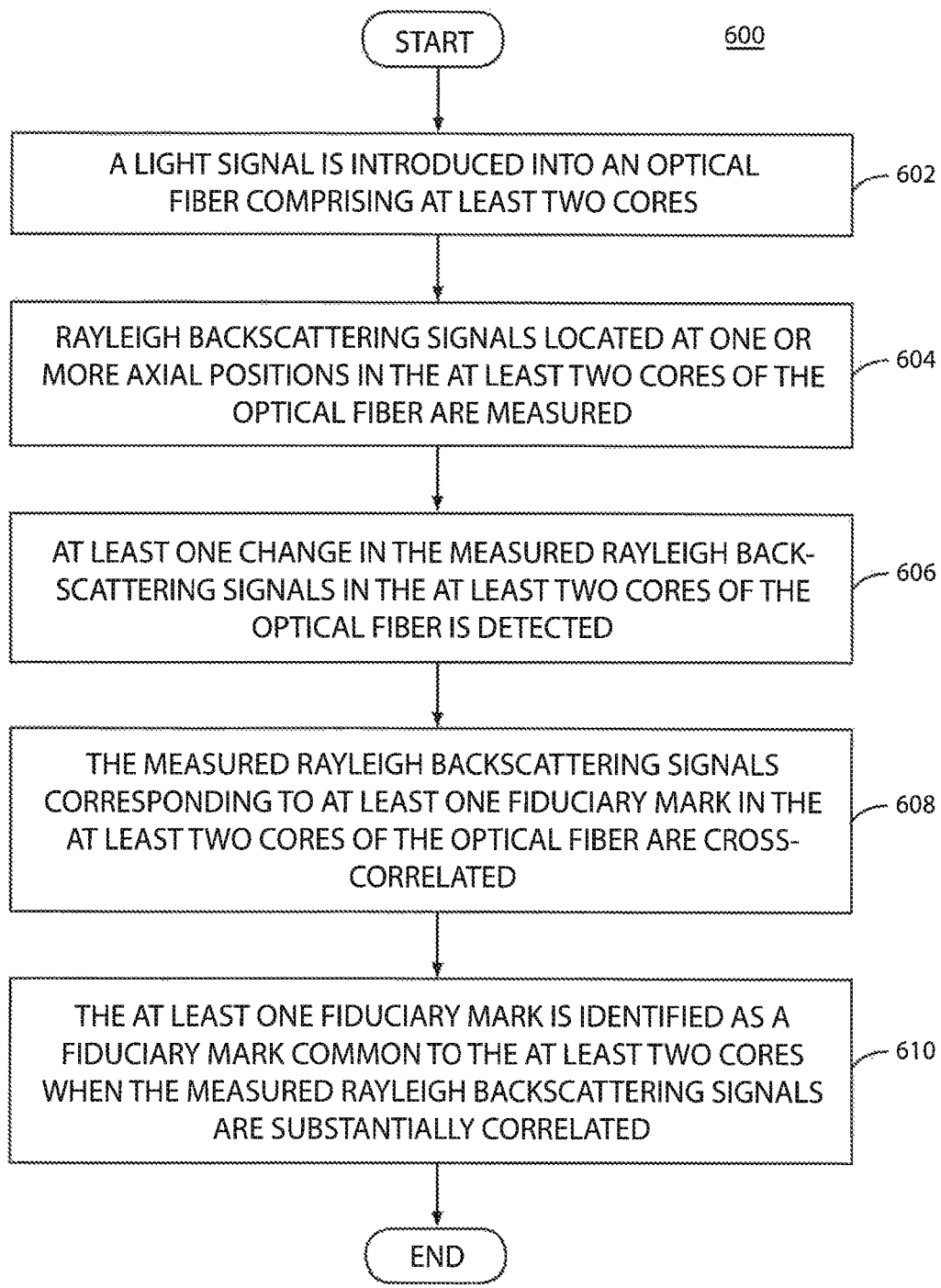

FIG. 6 is a process flow detailing a method of sensing a location in an optical sensor 100. Referring to FIGS. 1, 2 and 6, at block 602, a source of light 108 is introduced into an optical fiber 102 comprising at least two cores 112a-112n. At block 604, Rayleigh backscattering signals 106 located at one or more axial positions 110a-110n in the at least two cores 112a-112n of the optical fiber 102 are measured. At block 606, at least one change 202 in the measured Rayleigh backscattering signals 106 in the at least two cores 112a-112n of the optical fiber 102 are detected. At block 608, the measured Rayleigh backscattering signals 106 corresponding to at least one fiduciary mark (e.g., 104a) in the at least two cores 112a-112n of the optical fiber 102 are cross-correlated. At block 610, the at least one fiduciary mark (e.g., 104a) is identified as a fiduciary mark common to the at least two cores 112a-112n when the measured Rayleigh backscattering signals 106 are substantially correlated.

In an example, the at least one change 202 may be an abrupt change in the measured backscattering signals 106. In an example, the optical fiber 102 may have more than one core (e.g., 112a-112n) and the at least one fiduciary mark (e.g., 104a) may be marks at the same position in each core. In an example, the method may further comprise providing identifying information about a region where the at least one fiduciary mark (e.g., 104a) is located. The identifying information about a region where the at least one fiduciary mark (e.g., 104a) is located may identify a code indicating where the at least one fiduciary mark (e.g., 104a) is located.

It is to be understood that the exemplary embodiments are merely illustrative of the invention and that many variations of the above-described embodiments may be devised by one skilled in the art without departing from the scope of the invention. It is therefore intended that all such variations be included within the scope of the following claims and their equivalents.

What is claimed is:

1. A distributed sensor comprising an optical fiber having at least one fiduciary mark, the at least one fiduciary mark located at one or more axial positions along the optical fiber,
   the fiduciary mark comprising three or more individual marks of different length and spacing, or different backscattering response to incoming light and
   each individual mark configured to produce at least one change in the backscattering response to incoming light.

2. The distributed sensor of claim 1, wherein the backscattering signal is a Rayleigh backscattering signal.

3. The distributed sensor of claim 1, wherein the at least one fiduciary mark is placed in the fiber during the fiber manufacturing.

4. The distributed sensor of claim 1, wherein the at least one change is an abrupt change in the backscattering signal.

5. The distributed sensor of claim 1, wherein the at least one fiduciary mark is coded to provide information regarding the region where the fiduciary mark is located.

6. The distributed sensor of claim 5, wherein the coded information comprises digits of a number.

7. The distributed sensor of claim 1, wherein the at least one fiduciary mark is located at a known axial position along the optical fiber.

8. The distributed sensor of claim 1, wherein the at least one change in a backscattering signal is produced by an alteration to propagation properties of the optical fiber over substantially the same distance along the optical fiber.

9. The distributed sensor of claim 1, wherein the at least one change in a backscattering signal is a change in at least one of an intensity, amplitude, polarization dependence, or phase of the backscattering signal.

10. The distributed sensor of claim 1, wherein the alteration to propagation properties is an induced loss in the backscattering signal relative to a background noise signal.

11. The distributed sensor of claim 1, wherein the alteration to propagation properties is an induced gain in the backscattering signal relative to a background noise signal.

12. The distributed sensor of claim 1, wherein the at least one fiduciary mark is produced by exposure to actinic radiation.

13. The distributed sensor of claim 1, wherein the at least one fiduciary mark is produced by at least one of a thermal, an electrical, a strain, a poling, or a tapering perturbation of the optical fiber.

14. The distributed sensor of claim 1, wherein the at least one fiduciary mark the mark is made by splicing two or more fibers with different scattering strengths.

15. The distributed sensor of claim 1, wherein the at least one fiduciary mark is produced during a draw process of the optical fiber.

16. The distributed sensor of claim 1, wherein the at least one fiduciary mark is introduced in a core of the optical fiber.

17. The distributed sensor of claim 1, wherein the at least one-fiduciary mark is introduced in a cladding of the optical fiber.

18. The distributed sensor of claim 1, wherein the at least one fiduciary mark is configured to produce an aperiodic pattern, a quasi-periodic pattern, or a periodic pattern of altered backscattering.

19. The distributed sensor of claim 18, wherein individual parts of the aperiodic pattern, the quasi-periodic pattern, or the periodic pattern of altered backscattering comprise abrupt changes in backscattering.

20. The distributed sensor of claim 1, wherein the at least one fiduciary mark is configured to produce at least one change in a fiber Rayleigh backscatter.

21. The distributed sensor of claim 20, wherein the change in a fiber Rayleigh backscatter is made by exposing a section of the fiber to a single actinic beam.

22. The distributed sensor of claim 21, wherein the section of the fiber exposed to the single actinic beam is greater than 20 microns long longitudinally.

* * * * *